United States Patent [19]

Bohn et al.

[11] 4,191,533
[45] Mar. 4, 1980

[54] PREGNANCY-SPECIFIC $\beta_1$-GLYCOPROTEIN AND PROCESS FOR ISOLATING IT

[75] Inventors: Hans Bohn, Marburg; Ferdinand Stutzinger, Bretzenheim, both of Fed. Rep. of Germany

[73] Assignee: Behringwerke Aktiengesellschaft, Marburg an der Lahn, Fed. Rep. of Germany.

[21] Appl. No.: 858,890

[22] Filed: Dec. 9, 1977

Related U.S. Application Data

[60] Continuation-in-part of Ser. No. 842,163, Oct. 14, 1977, abandoned, which is a division of Ser. No. 569,476, Apr. 18, 1975, Pat. No. 4,065,445, which is a continuation-in-part of Ser. No. 292,735, Sep. 27, 1972, abandoned.

[30] Foreign Application Priority Data

Sep. 29, 1971 [DE] Fed. Rep. of Germany ....... 2148587
Nov. 20, 1971 [DE] Fed. Rep. of Germany ....... 2157610

[51] Int. Cl.$^2$ .................. G01N 33/16; A23J 1/06; A61K 39/00
[52] U.S. Cl. .................. 23/230 B; 260/112 B; 424/12; 424/101; 424/105
[58] Field of Search .................. 260/112 R, 112 B; 424/12, 101, 105; 23/230 B

[56] References Cited

U.S. PATENT DOCUMENTS

| | | | |
|---|---|---|---|
| 3,310,471 | 3/1967 | Parcells et al. | 424/105 |
| 3,446,598 | 5/1969 | Yoder et al. | 260/112 R |
| 3,687,833 | 8/1972 | Parcells et al. | 260/112 R |
| 3,883,304 | 5/1975 | Hamilton | 23/230 B |
| 4,065,445 | 12/1977 | Bohn et al. | 260/112 B |

FOREIGN PATENT DOCUMENTS

2543994 7/1977 Fed. Rep. of Germany ............. 424/88

OTHER PUBLICATIONS

Bohn, Chemical Abstracts, vol. 77:59,673q (1972, effective date 5/72).
Bohn, Chemical Abstracts, vol. 76:70,559g (1972, effective date 1971).
Gottschalk, Glycoproteins, (1966), pp. 362–377, 446–455, 537, 538, 558–562.
Chemical Abstracts, Subject Index, pp. 141,565–141,570 (1967–1971).
Centonze et al., Chemical Abstracts, vol. 51:16,804e (1957).
Boenisch et al., Chemical Abstracts, vol. 74:62,320r (1971).
Centonze et al., Chemical Abstracts, vol. 55:23,724f; 23,725a (1961).
Bohn, Chemical Abstracts, vol. 78:95,495n (effective date–1972), (1973).
Higashi, Chemical Abstracts, vol. 57:10,481d (1962).
Bohn and Zwisler, Chemical Abstracts, vol. 77:118,184f, 118,185g (1972).
Mansfield et al., Chemical Abstracts, vol. 59:9157a (1963).
Bohn, Chemical Abstracts, vol. 76:32,096w (1972, effective date 1971).

*Primary Examiner*—Walter C. Danison
*Attorney, Agent, or Firm*—Curtis, Morris & Safford

[57] ABSTRACT

A pregnancy-specific $\beta_1$-glycoprotein, characterized by an electrophoretic migration speed in agar gel in the range of the $\beta_1$-globulins, a sedimentation constant of 4.6 S±0.5 S, a molecular weight of 100 000±15 000, an extinction coefficient $E_{1cm}^{1\%}$ of 11.6±0.5 (278 mμ; 1/15-molar phosphate buffer, pH 7.0), a carbohydrate content of 28.05±1.55%, comprising 10.7±1.0% of hexoses, 10.0±0.5% of hexosamine, 0.55±0.05% of fucose and 7.0±0.5% of neuraminic acid, and process for isolating it from the placenta or blood or urine of pregnant women. This protein may be used as a reagent and for the preparation of antisera as reagents for the detection of pregnancy and for pre-natal supervision.

1 Claim, No Drawings

PREGNANCY-SPECIFIC $\beta_1$-GLYCOPROTEIN AND PROCESS FOR ISOLATING IT

This application is a continuation-in-part application of application Ser. No. 842,163 filed Oct. 14, 1977, now abandoned, which is a divisional application of application Ser. No. 569,476 filed Apr. 18, 1975, now U.S. Pat. No. 4,065,445, which, in turn, is a continuation-in-part application of application Ser. No. 292,735 filed Sept. 27, 1972 and now abandoned, all applications having been filed by Hans Bohn and Ferdinand Stutzinger for PREGNANCY-SPECIFIC $\beta_1$-GLYCOPROTEIN AND PROCESS FOR ISOLATING IT.

This invention relates to a pregnancy specific $\beta_1$-glycoprotein and to a process for isolating it.

It has not been known hitherto that the placenta and the urine of pregnant women contain a pregnancy-specific $\beta_1$-glycoprotein. Although a protein in the $\beta$-range has already been proved immunologically in the serum of pregnant women, a process for isolating it has not yet been described.

The object of the invention is a process for isolating the pregnancy-specific $\beta_1$-glycoprotein (abbreviated $SP_1$) by fractionation from the placenta and the blood or urine of pregnant women. Another object of the invention is the pregnancy-specific $\beta_1$-glycoprotein which is characterized by an electrophoretic migration speed in agar gel in the range of the $\beta_1$-globulins, a sedimentation constant of 4.6 S±0.5 S, a molecular weight of 100 000±15 000, an extinction coefficient $E_1$ $cm^{1\%}$ of 11.6±0.5 (278 m$\mu$; 1/15-molar phosphate buffer, pH 7.0), a carbohydrate content of 28.05±1.55%, comprising 10.7±1.0% hexoses, 10.0±0.5% of hexosamine, 0.55±0.05% of fucose and 7.0±0.5% of neuraminic acid.

An analytical amino acid assay of the pregnancy specific $\beta_1$-glycoprotein was carried out according to the method of Moore et al. (Anal. Chem. 30 (1958) 1185) using the liquid chromatograph Multichrom B (Fa. Beckmann) and the ion exchange resins M 71 and M 82. Cystine (half) was determined as cysteic acid after oxidation of the proteins with performic acid (S. Moore; J. Biol. Chem. 238 (1963) 235) and subsequent chromatography as mentioned before.

Tryptophan was determined with the direct photometric method according to H. Edelhoch (Biochemistry 6 (1967) 1948.

The analytical amino acid assay of the pregnancy specific $\beta_1$-glycoprotein shows the following composition:

| | Amino acid residues per 100 amino acids | |
|---|---|---|
| Amino acid | mean | double standard deviation (+ 2 S) |
| Lysine | 4.37 | ± 0.28 |
| Histidine | 1.77 | ± 0.07 |
| Arginine | 5.07 | ± 0.22 |
| Aspartic acid | 9.85 | ± 0.17 |
| Threonine | 8.24 | ± 0.39 |
| Serine | 9.07 | ± 0.55 |
| Glutamic acid | 8.97 | ± 0.22 |
| Proline | 7.96 | ± 0.31 |
| Glycine | 7.07 | ± 0.83 |
| Alanine | 3.74 | ± 0.33 |
| Cystine (half) | 1.57 | ± 0.14 |
| Valine | 5.84 | ± 0.32 |
| Methionine | 0.88 | ± 0.19 |
| Isoleucine | 5.79 | ± 0.40 |
| Leucine | 9.60 | ± 0.28 |
| Tyrosine | 5.75 | ± 0.20 |
| Phenylalanine | 2.12 | ± 0.21 |
| Tryptophan | 2.39 | ± 0.70 |

The ranges given for the amino acid contents in the above table are mainly due to the imprecision of the analytical method and not to a non-uniformity or contamination of the product submitted to analysis.

The pregnancy-specific $\beta_1$-glycoprotein of the invention serves for the preparation of antisera. The essence of the process for preparing the anti-pregnancy-specific $\beta_1$-glycoprotein serum resides in the fact that animals may be immunized according to known methods with the pregnancy-specific $\beta_1$-glycoprotein which is described below, and the antiserum is obtained from the blood of the animals.

The process of the invention therefore permits obtaining novel antisera according to known methods of animal immunization.

A further object of the present invention is a diagnostic agent for the detection and supervision of a pregnancy, which contains the anti-pregnancy-specific $\beta_1$-glycoprotein obtainable according to the process as described above.

With the antisera, a pregnancy can be proved by immunological methods (hemagglutination—inhibition test, complement binding reaction, radio-immuno-assay, latex agglutination). The proof can be carried out with the serum or urine of the pregnant woman. A quantitative determination of $SP_1$, for example by radial immuno-diffusion, may become important for pre-natal supervision.

A further object of the present invention is a diagnostic agent for the detection and supervision of a pregnancy, which contains as essential component the $\beta_1$-glycoprotein.

Because it is pregnancy-specific the novel $\beta_1$-glycoprotein contained as essential component in the diagnostic agent in accordance with this invention is called hereinafter pregnancy-specific $\beta_1$-glycoprotein and $SP_1$ in abbreviated form.

The diagnostic agent of the invention may be used for the qualitative or quantitative detection of the $\beta_1$-glycoprotein. Since the quantitative relation can often be established only by means of a standardized antigen product, a corresponding diagnostic agent in accordance with this invention is required, by means of which a relation diagram may be established. Thus, the antigen concentration is determined in the samples to be tested.

A further example of cases where the specific antibody as well as the diagnostic agent of the invention is required is the radio-immuno-assay. For this quantitative determination method of antigens, radioactively marked $SP_1$ and the specific antibody must be used. Furthermore, a diagnostic agent in accordance with this invention is required for establishing a relation diagram.

The detection may be carried out with serum or urine of the pregnant woman. A quantitative determination of $\beta_1$-glycoprotein, for example by radial immunodiffusion, may be important for the supervision of a pregnancy.

For preparing the pregnancy-specific $\beta_1$-glycoprotein, comminuted placentas are extracted with water or a weak salt solution. A weak salt solution in the sense of the invention means an aqueous solution of one or more physiologically compatible salts having an overall concentration not essentially below or above that of a so-called physiological saline solution. Accordingly, suitable concentrations range between 0.1 and 5% by weight of solution. Suitable salts are those which are usually used in the aqueous extraction of tissue material, preferably sodium chloride, sodium phosphate, sodium citrate, tris(oxymethyl)-aminomethane/hydrochloric acid, glycine/hydrochloric acid.

The aqueous extract thus obtained or the blood serum, or urine of pregnant women is then precipitated at an acid, neutral or weakly alkaline pH by addition of acridine or quinoline or of a derivative thereof.

The most preferred pH for the precipitation is pH 7-8 with acridine derivatives and 5-6 with quinoline derivatives. However, higher or lower pH values can be used with almost the same success so long as they are in the range between pH 5 and pH 9.

As acridine or quinoline compounds used in the present invention there are suitable, in addition to the basic compounds per se, the derivatives obtained from them by substitution. The substituent may be alkyl, alkoxy and/or amino groups in various positions. Since the acridine and quinoline bases are sparingly soluble in an aqueous medium it is preferred to use slightly water-soluble salts. E.g. 2-ethoxy-6.9-diamino-acridine, preferably in the form of its lactate, and bis-(2-methyl-4-amino-quinolyl-6) -carbamide suitably in the form of its hydrochloride, have proved especially suitable.

The acridine or quinoline compound is added to the placental extract or body fluid in form of an aqueous solution. The concentration of the acridine or quinoline compounds in the final stage shall be between 0.2 and 1.0% by weight calculated on the volume of the solution.

The acridine or quinoline compound should act on the extract or the body fluid for a period of time which gives the components sufficient opportunity to react and to form a precipitate. In general, a contact time of about 10 to 30 minutes is sufficient. Longer times may be used without hesitation. A shorter contact time is not advisable, although under certain circumstances it may also give good results.

The preferred temperature is room temperature, i.e. 20° to 25° C., but higher or lower temperatures in the range between 0° C. and 40° C. will be suitable, too.

The contact of the liquid with the acridine or quinoline compound can be improved by intensive mixing, for example by stirring.

The precipitate that forms, i.e. the first precipitate in this process, is then separated from the solution. This can be done in known manner, for example by decantation, filtration or preferably, by centrifugation. The precipitate is discarded. In the remaining liquid containing the SP$_1$, the precipitating agent which is not bound in the precipitate can be removed, if desired, according to known methods, for example by adsorption on suitable adsorbing agents such as silica gel, bentonite, active charcoal or by precipitation with alkali metal halides. After separation of the adsorbing agent or of the precipitate formed by precipitation of the excess acridine or quinoline compound, which separation is carried out according to the above described known methods, or even directly after separating the first precipitate, the SP$_1$ remaining in the supernatant is precipitated together with gamma-globulin by salt addition. For this purpose an inorganic physiologically acceptable salt, e.g. ammonium sulfate, potassium phosphate is added as a solid to the liquid up to a salt concentration of 50% calculated on the volume of solution. After standing for a while, a precipitate (the second precipitate in this process) is formed. It contains the SP$_1$ together with the main quantity of gamma-globulin. This second precipitate is collected by a suitable method, e.g. decantation, filtration or centrifugation, and is dissolved in a suitable aqueous solvent for further separation of the SP$_1$. This solvent may be pure water. More suitably, however, the solvent is one of the known saline or buffer solutions used in the isolating procedures for proteins. Especially suitable solvents in this stage of the process are tris-(oxymethyl)-aminomethane/hydrochloric acid buffer solutions or sodium phosphate buffer solutions.

The solvent is used in an amount sufficient to dissolve the whole second precipitate. A slight excess of the solvent is not deleterious. However, a large excess should be avoided. The solution thus obtained, if desired, is dialyzed against a saline or buffer solution for further purification.

Subsequently the SP$_1$ is adsorbed from this dialyzed solution on an ion exchanger, preferably an anion exchanger such as diethylaminoethyl (DEAE)-cellulose. The adsorption may be carried out in known manner in a batch process or continuously in a column.

After adsorption, the SP$_1$ is eluted from the exchanger with a weakly acid buffer solution, e.g. a tris-oxymethylaminomethyl-hydrochloric acid buffer, preferably of pH 6.5. Generally, all buffer solutions having pH values between 2.0 and 9.0 are suitable for elution. The buffer solution may contain as additional ingredients physiologically compatible neutral salts such as sodium chloride in concentrations between 0.1–10% and/or stabilizers, e.g. alkali metal azides, in amounts ranging from 0.01 to 0.2%. The eluate may be precipitated again by salt addition, e.g. by ammonium sulfate, whereby the SP$_1$ is obtained in enriched form.

It can be further purified by a molecular sieving method like ultrafiltration or gel filtration, for example with the aid of Sephadex ® G-150. For further purification, preparative zone electrophoresis with PVC as carrier in a suitable buffer solution, preferably in a solution containing voltaile buffer salts, for example 0.075% ammonium-bicarbonate, may be used. After the electrophoretic separation, the SP$_1$-containing $\beta$-zone of the carrier is cut out, eluted with ammonium-bicarbonate and lyophilized. Other suitable fine purification methods comprise chromatographing on DEAE-Sephadex and subsequent elution with a sodium chloride gradient, and fractionation with alcohol, preferably with ethanol. The pregnancy-specific $\beta_1$-glycoprotein is isolated in similar manner from the blood or urine of pregnant women.

In addition to the fractionation steps that take advantage of its precipitation behavior and its electric charge, the pregnancy-specific $\beta_1$-glycoprotein may be obtained by a process which is based on the interaction between the pregnancy-specific $\beta_1$-glycoprotein and the antibodies obtainable therefrom. In this process, the pregnancy-specific $\beta_1$-glycoprotein is removed from its solutions by specific immune adsorption on a carrier containing an insoluble antibody to pregnancy-specific $\beta_1$-glycoprotein, and eluted thereafter.

An antibody that can be bound according to known processes to a solid carrier can be prepared by immunization of animals with the $SP_1$, for example the product obtained according to Example 3, recovering blood from the so-immunized animals and isolating in known manner the immunoglobulin fraction from the serum of this blood.

The thus obtained anti-$SP_1$ serum is bound to a suitable carrier according to known methods as described, e.g. in Cuatrecasas, P., Ann. Rev. Biochem 40, 259 (1971); Feinstein, G., Naturwissenschaften 58, 389 (1971) or Axen, R. et al., Nature 214, 1302 (1967). Suitable carriers are high polymer carbohydrates such as cellulose or agar, synthetic resins, for example polyacrylamide or ethylene-maleic acid anhydride-copolymers, or even glass particles.

A preferred carrier material is purified agarose in the form of small spheres of a diameter of about 20–200 $\mu$m, to which antibodies against pregnancy-specific $\beta_1$-glycoprotein may be bound covalently according to the method of Axen, inter alia.

For the isolation of the pregnancy-specific $\beta_1$-glycoprotein, a solution which contains still other proteins or carbohydrate impurities in addition to pregnancy-specific $\beta_1$-glycoprotein, for example a placental extract or serum or urine of pregnant women, is brought into contact with the specific anti-pregnancy-specific $\beta_1$-glycoprotein adsorbent, the pH of the solution being adjusted to >4. Because the upper pH value is limited by denaturation phenomena of the protein, it is advantageous to choose the pH within the range from 4 to 9. The salt concentration of this solution is not critical. Conditions that are known to dissolve antigen-antibody-bonds must be avoided. Advantageously, the aqueous solution contains neutral salts and/or buffer substances commonly used in biochemistry, especially sodium chloride, phosphates suitable as buffer substances, tris-hydroxy-methyl-aminomethane or buffer substances that are enumerated by Good et al., Biochemistry 5, 472 (1966), preferably in a concentration range of 0.01–0.2 M/l. The ratio of protein solution to adsorbent is advantageously within the range from 1:1 to 1:1, preferably 2:1. After the adsorbent has been in contact with the pregnancy-specific glycoprotein solution for 0.1 to 5 hours, the pregnancy-specific $\beta_1$-glycoprotein is specifically bound to the antibodies. The adsorbent is then separated from the solution by centrifugation or by filtration and washed several times with a neutral salt solution to eliminate excess salts and unspecifically adsorbed impurities.

The elution of the pregnancy-specific $\beta_1$-glycoprotein can be carried out using measures which are known for their capability of dissolving antigen-antibodies.

Thus the elution can be carried out using a solution having a pH value of <4, preferably within the range of from 2 to 4. This procedure is effected by contacting the adsorbent bearing the $SP_1$ with a weakly concentrated aqueous salt or buffer solution, preferably one containing 0.2 to 8 moles per liter of neutral salts or buffer substances. Most simply a dispersion of the adsorbent in the solution is stirred for 0.1 to 2 hours, whereupon the pregnancy-specific $\beta_1$-glycoprotein is desorbed from the immune adsorbent. After separation of the adsorbent the solution containing the pregnancy-specific $\beta_1$-glycoprotein is adjusted to a pH near the neutral point, i.e. between 6 and 8. Thereafter further purification, for example with hydroxylapatite may follow, if desired.

Likewise the elution can be carried out by the use of solutions of protein-dissociating agents, for example urea solutions or solutions of so-called chaotropic salts, for example $NaNO_3$, $NaBr$, $NaClO_4$, $CF_3COONa$, $NaSCN$ and $CCl_3COONa$ having a molarity of 0.2 to 9 m/l.

To remove the chaotropic salts from the solution after desorption of the pregnancy-specific $\beta_1$-glycoprotein and separation of the adsorbent, the solution is dialyzed against a neutral salt or buffer solution having a concentration between 0.1–1 M/l. Further purification may follow also in this case, for example with hydroxyl apatite as described below.

Generally, the pregnancy-specific $\beta_1$-glycoprotein obtained according to the process steps described has a degree of purity within the range of from 90 to 95%.

An especially adequate method of highly purifying the product is an adsorption step using a hydroxyl apatite suspension as adsorbent and choosing the adsorption conditions such that the pregnancy-specific $\beta_1$-glycoprotein is not adsorbed, but only the impurities still present are bound by the hydroxyl apatite.

It is essential that the adsorption takes place in an aqueous medium containing phosphate ions, preferably in a buffer solution containing phosphate ions, for example a solution of potassium phosphate or sodium phosphate in a pH range of 6 to 8 and with 0.001 to 0.01 moles phosphate ions. For the adsorption of the impurities, batch processes as well as column chromatography are suitable. According to these processes, the pregnancy-specific $\beta_1$-glycoprotein is obtained in a purity of above 99%.

The following Examples illustrate the invention:

EXAMPLE 1

Isolation from placentas 150 kg of deep-frozen placentas were comminuted and extracted with 150 liters of a 0.5% aqueous solution of sodium chloride. The extract was adjusted to pH 8 by means of 2 N-sodium hydroxide and combined with 50 liters of a 3% aqueous solution of diaminoethoxyacridine lactate (Rivanol ®). After 1 hour the supernatant, which contained the $SP_1$ together with gamma-globulin, was siphoned off from a first precipitate which had formed, combined with 5% of solid sodium chloride (11 kg) in order to separate the Rivanol which still had remained in solution, filtered and combined with 26.5%, referred to the weight of the liquid, of solid ammonium sulfate and well stirred. After 1 hour the precipitate which formed was filtered off.

500 g of the precipitate that had deposited on the filter were dissolved in 500 ml of distilled water and dialyzed against a 0.01 molar tris-(oxymethyl)-aminomethane (hereinafter referred to as "tris")/hydrochloric acid buffer solution having a pH-value of 7.0 and containing 0.05% of sodium azide. The dialyzed solution was centrifuged and the supernatant was filled up with the same buffer solution to a volume of 2000 ml, the pH-value was adjusted to 8.0 by means of 0.1 N sodium hydroxide solution and stirred with 250 g of wet DEAE-cellulose for 1 hour.

The DEAE cellulose was then separated by filtration from the solution, washed twice with 1 liter portions of 0.01-molar tris/hydrochloric acid buffer having a pH-value of 8.0 and then eluted thrice with 500 ml portions of a 0.02-molar tris/hydrochloric acid buffer having a pH-value of 6.5 and containing 0.85% of sodium chloride and 0.05% of sodium azide. The combined eluates were combined with 30% of ammonium sulfate, referred to the weight of the liquid, and the whole was stirred. The precipitate which contained the $SP_1$ was dissolved in 300 ml of distilled water and subjected to gel filtration by means of Sephadex G-150 and using a 0.1-molar tris/hydrochloric acid buffer having a pH-value of 8.0 and containing, per liter, 1.0 mole of sodium chloride (100:20 cm column).

The eluates were then tested with specific $SP_1$-antiserum, the $SP_1$-containing fractions were collected and the proteins were precipitated again therefrom as described above with the aid of 30% solid ammonium sulfate.

A further purification was effected by preparative zone electrophoresis with polyvinyl chloride (PVC) as carrier. As buffer, a 0.075-molar ammonium-bicarbonate solution (pH 8.0) was used. After the electrophoretic separation, the $SP_1$-containing $\beta$-zone was cut out, eluted with the ammonium-bicarbonate buffer and the eluates were lyophilized.

The dry substance was dissolved in a 0.01-molar tris/hydrochloric acid buffer having a pH-value of 7.0 and containing 0.2% of sodium chloride, chromatographed on DEAE-Sephadex (column 5×20 cm) and eluted with a linear gradient of 0.2 to 2.0% of sodium chloride in a 0.01-molar tris/hydrochloric acid buffer having a pH-value of 7.0. Then, precipitation with 40% ethanol was carried out at $-5°$ C. After the precipitate was separated by centrifugation, the supernatant was dialyzed against distilled water until it was free from salt and lyophilized. Purity 90 to 95%. This preparation could be used for the manufacture of antisera.

EXAMPLE 2

Isolation from blood 5 liters of the serum of pregnant women were diluted with distilled water in a ratio of 1:1 and the main quantity of the plasma proteins was precipitated therefrom with the aid of 2.5 liters of 3% of Rivanol at a pH-value of 8.0. For removing the Rivanol, the supernatant obtained by centrifugation was combined with 5% of sodium chloride. The resulting precipitate was removed by centrifugation and the supernatant was separated from the sediment and combined with 30% of solid ammonium sulfate. The precipitate contained the gamma-globulin and the pregnancy-specific $\beta_1$-glycoprotein. The precipitate was dissolved in a 0.01-molar tris/hydrochloric acid buffer having a pH-value of 7.0, dialyzed against a 0.01-molar tris/hydrochloric acid buffer having a pH-value of 7.0 and then purified with DEAE-cellulose. The treatment on DEAE-cellulose was carried out in a 0.01-molar tris/hydrochloric acid buffer having a pH-value of 8.0. Elution from the DEAE-cellulose, gel filtration with Sephadex and precipitation with alcohol were carried out as described in Example 1.

EXAMPLE 3

Isolation of pregnancy-specific $\beta_1$-glycoprotein from its solution by immune adsorption An immune adsorbent suitable for specifically binding pregnancy-specific $\beta_1$-glycoprotein was prepared by binding 1.75 g of protein of an immunoglobulin fraction obtained from anti-pregnancy-specific $\beta_1$-glycoprotein rabbit serum to 175 g of Sepharose (registered trade mark) 4 B, (cf. Handbook of Biochemistry, selected data for molecular Biology, Edited by Herbert A. Sober, 2nd Edition, 1970, page K 73) that was activated with 21.8 g of BrCN (cf. Axen R., Porath, J., Ernbach, S.: Nature 214, 1302 (1967)). By means of this immunoadsorbent, pregnancy-specific $\beta_1$-glycoprotein was isolated from the extract of placentae according to the following process:

1 liter of a placental extract containing pregnancy-specific $\beta_1$-glycoprotein, the protein content of which is 5%, is dialyzed against 10 liters of 0.1 molar trishydroxymethyl-aminoethanehydrochloric acid buffer (pH 8) which contains 1 mole/l of NaCl and 1 g/l of sodium azide. Thereafter the adsorbent as obtained above is added to this solution, the solution is stirred at 4° C. for 2 hours and the adsorbent is suction-filtered together with the bound pregnancy-specific $\beta_1$-glycoprotein. The adsorbent is washed with 2×250 ml of 0.1 molar trishydroxymethylaminomethanehydrochloric acid-buffer solution and then with 2×250 ml of a physiological sodium chloride solution (0.9%); then the adsorbent is treated six times for 20 minutes each with 400 ml portions of a 0.5 molar glycine-HCl buffer of pH 2.5. The combined eluates are adjusted to pH 7 with 1 N NaOH and concentrated to 10 ml on an ultrafilter. The concentrate is dialyzed against a 0.005 molar sodium phosphate buffer of pH 6.8 and further purified by chromatography on hydroxyl-apatite as described in Example 4.

The same process can be used when the pregnancy-specific $\beta_1$-glycoprotein is to be obtained from the serum or the urine of pregnant women.

EXAMPLE 4

For highly purifying pregnancy-specific $\beta_1$-glycoprotein, 50 mg of the product obtained according to Examples 1 or 2, having a purity of 90–95%, were dissolved in 10 ml of 0.005 molar sodium phosphate buffer (pH 6) and applied to a column of a dimension of 2×8 cm filled with hydroxyl-apatite (Messrs. Serva, Heidelberg) which had been equilibrated before with 0.005 molar phosphate buffer. Upon eluting the substance with 0.005 molar phosphate buffer, the pregnancy-specific $\beta_1$-glycoprotein migrates through the column, whereas the impurities remain adsorbed on the hydroxylapatite. The protein-containing eluate was dialyzed against 10 times its volume of water to eliminate the salts and then lyophilized. Yield of pregnancy-specific $\beta_1$-glycoprotein about 40 mg; degree of purity: >99%. That is according to immunological processes, none of the admixtures ascertained before purification could be reascertained.

EXAMPLE 5

Preparation of an antiserum

For the preparation of a specific antiserum, rabbits are immunized within 6 weeks with the purified pregnancy-specific $\beta_1$-glycoprotein, while using aluminum hydroxide as an additive.

The pregnancy-specific $\beta_1$-glycoprotein is dissolved in a physiological saline solution (concentration 0.06 mg/3 ml) and, with addition of aluminum hydroxide, stirred to form a suspension. 0.06 mg each of protein in 3 ml of suspension per animal are administered to the rabbits for 5 consecutive days by intravenous injection. Subsequently, the animals are not treated any more for 9 days. Immunization is then started again for 5 consecutive days with the above amount of antigen, the animals are left to themselves for a further 9 days, and finally, a further 0.06 mg each of the antigen is injected on 5 consecutive days. After another period of 7 to 9 days, the animals are bled. After coagulation of the blood, the serum is centrifuged off from the coagulum, and thus obtained.

EXAMPLE 6

Composition of a diagnostic agent

A test arrangement for the immunologic determination of the pregnancy-specific $\beta_1$-glycoprotein consists of anti-pregnancy-specific $\beta_1$-glycoprotein serum of rabbits, and a reference standard for the pregnancy-specific $\beta_1$-glycoprotein. This latter reference standard is obtained by dissolving a determined amount of the purified protein in human serum, stored human serum or a plasma substitute solution as stabilizing solvent. The concentration is advantageously chosen in such a manner that it corresponds to about 25 to 36 mg of pregnancy-specific $\beta_1$-glycoprotein per 100 ml.

EXAMPLE 7

Quantitative determination of the pregnancy-specific $\beta_1$-glycoprotein 1 g of agarose is mixed with 50 ml of diethylbarbiturate-acetate buffer solution having a pH of 8.6 and an ionic strength of 0.04 M, 50 ml of distilled water and 10 g of thiocide stabilizer, and the whole is heated to about 100° C. until a clear solution has formed. By means of a prewarmed graduated pipette, 15 ml of this solution are poured onto a glass plate having a size of 10×10 cm and being in an absolutely horizontal position. After having been allowed to stand for a short time at room temperature, the solution solidifies to a transparent gel layer having a uniform thickness. At a distance of 2 cm from the rim of the glass plate, hollows having a diameter of 4 mm are punched, which serve for the sera of women to be tested and the solutions used as relation standard containing 4, 8, 16 and 32 mg of $SP_1$/100 ml. 15 μl of the solutions to be tested are filled into the hollows, and left for 3 hours in a moisture chamber. Subsequently, the agarose layer is cut at a distance of 0.5 cm starting from the hollows, and removed from the glass plate. That part of the plate laid bare is now coated with 15 ml of an agarose solution prepared as described above and to which, on cooling to 50° C., anti-$SP_1$ serum had been added until a concentration of 1.5% was attained. Subsequently to this coating, the samples applied to the hollows are separated by electrophoresis into the adjacent antiserum-containing gel during 15 hours at 2 volts/cm. The gels are then washed and dried according to usual electrophoresis methods, and the immunoprecipitate lines formed during the electrophoresis are dyed with amido-black in order to make them more clearly visible. The height of the precipitate peaks is a measure for the concentration of $SP_1$ in the tested samples, and it is put into relation to the precipitate peaks of the standard solutions. In the present test, there was no formation of precipitate in the case of a serum of a non-pregnant woman. In that of a women being in the 8th week of pregnancy, 1 mg of $SP_1$ was contained in 100 ml of serum. The serum of a woman pregnant for 20 weeks contained 5 mg of $SP_1$ per 100 ml, and that of a woman pregnant for 32 weeks contained 20 mg of $SP_1$ per 100 ml.

We claim:

1. A method for detecting the presence of a pregnancy-specific $\beta_1$-glycoprotein in the blood or urine of a female animal or woman, whereby a pregnancy can be detected and supervised, which comprises contacting a sample of the blood or urine to be tested with antiserum to said pregnancy-specific $\beta_1$-glycoprotein and examining the sample for evidence of an immune reaction, said pregnancy-specific $\beta_1$-glycoprotein having an electrophoretic migration speed in agar gel in the range of $\beta_1$-globulins, a sedimentation constant of 4.6 S±0.5 S, a molecular weight of about 100 000±15 000, an extinction coefficient $E_1$ $_{cm}^{1\%}$ of 11.6±0.5 (278 mμ; 1/15-molar phosphate buffer, pH 7.0), and a carbohydrate content of 28.05±1.55%, comprising 10.7±1.0% of hexoses, 10.0±0.5% of hexosamine, 0.55±0.05% of fucose, and 7.0±0.5% of neuraminic acid.

* * * * *